(12) United States Patent
Austin

(10) Patent No.: US 11,653,655 B2
(45) Date of Patent: May 23, 2023

(54) IMPROVING THE ROLLABILITY OF FLAT BREADS

(71) Applicant: Novozymes A/S, Bagsvaerd (DK)

(72) Inventor: Dilek Austin, Wake Forest, NC (US)

(73) Assignee: Novozymes A/S, Bagsvaerd (DK)

( * ) Notice: Subject to any disclaimer, the term of this patent is extended or adjusted under 35 U.S.C. 154(b) by 627 days.

(21) Appl. No.: 16/316,090

(22) PCT Filed: Jun. 29, 2017

(86) PCT No.: PCT/EP2017/066146
§ 371 (c)(1),
(2) Date: Jan. 8, 2019

(87) PCT Pub. No.: WO2018/010966
PCT Pub. Date: Jan. 18, 2018

(65) Prior Publication Data
US 2021/0282411 A1    Sep. 16, 2021

Related U.S. Application Data

(60) Provisional application No. 62/362,642, filed on Jul. 15, 2016.

(51) Int. Cl.
*A21D 8/04* (2006.01)
*A21D 13/42* (2017.01)
*A21D 13/047* (2017.01)
*A21D 10/00* (2006.01)

(52) U.S. Cl.
CPC ........... *A21D 8/042* (2013.01); *A21D 10/005* (2013.01); *A21D 13/047* (2017.01); *A21D 13/42* (2017.01); *C12Y 302/01001* (2013.01); *C12Y 302/01002* (2013.01)

(58) Field of Classification Search
CPC ........ A21D 8/042; A21D 13/42; A21D 13/43; A21D 13/047; A21D 10/005; C12Y 302/01001; C12Y 302/01002
USPC ..................................................... 426/18, 28
See application file for complete search history.

(56) References Cited

U.S. PATENT DOCUMENTS

| | | |
|---|---|---|
| 2003/0059496 A1 | 3/2003 | Rubio |
| 2003/0165593 A1* | 9/2003 | Johansen ............... A23L 7/117 426/18 |
| 2009/0142465 A1 | 6/2009 | Sturkenboom et al. |
| 2011/0059491 A1 | 3/2011 | Matsunaga et al. |
| 2012/0034343 A1 | 2/2012 | Mikkelsen et al. |
| 2012/0121760 A1 | 5/2012 | Matsunaga |
| 2013/0273198 A1 | 10/2013 | Salomonsen et al. |
| 2016/0113295 A1 | 4/2016 | Forman et al. |

FOREIGN PATENT DOCUMENTS

| | | | |
|---|---|---|---|
| EP | 1541028 A1 * | 6/2005 | ............... A21D 2/36 |
| EP | 1541028 A1 | 6/2005 | |
| GB | 2417184 A | 2/2006 | |
| WO | 1991/04669 A1 | 4/1991 | |
| WO | 2004/081171 A2 | 9/2004 | |
| WO | 2010/124206 A1 | 10/2010 | |
| WO | 2016/030448 A1 | 3/2016 | |

OTHER PUBLICATIONS

Arora, s. The effect of enzymes and starch damage on wheat flour tortilla quality. A Thesis. Texas A & M university. (Year: 2003).*
Witkowski, A. et al. Biochemistry 38: 11-643-11650 (Year: 1999).*
Seffernick, J. J. Bacteriology. 183: 24-05-2410 (Year: 2001).*
Protein ID ADS 75878—Standard protein. Maltogenic alpha-amylase (Year: 2004).*
Protein ID AXS19850—Standard protein. Beta-amylase (Year: 2009).*
Web-Search-History (Year: 2021).*
Bueso, F. J. et al. Effect of temperature on texture of corn tortilla with and without antistaling additives. (Year: 2006).*
Austin, D. L. Enzymes Extending shelflife of eating quality of Tortillas. Tortillas, Wheat flour and corn products. pp. 201-214. (Year: 2015).*
Forman, 2011, Downloads from websites.
Li (ED), Handbook on the Nutritional Value of Processed Foods, p. 105 (1989).
Zheng et al., Food Enzymology, pp. 181-182 (2006).
Zhang ed, 2010, China Light Industry Press, 230.

* cited by examiner

*Primary Examiner* — Hamid R Badr
(74) *Attorney, Agent, or Firm* — Yoshimi Barron

(57) ABSTRACT

The present invention deals with a method for improving the rollability of flat breads comprising a) adding a maltogenic alpha-amylase and a beta amylase to a flour or directly to a dough comprising a flour; b) making the dough; and c) making flat breads from the dough.

10 Claims, No Drawings

Specification includes a Sequence Listing.

IMPROVING THE ROLLABILITY OF FLAT BREADS

CROSS-REFERENCE TO RELATED APPLICATIONS

This application is a 35 U.S.C. 371 national application of international application no. PCT/EP2017/066146 filed Jun. 29, 2017 and published as WO2018/010966 on Jan. 18, 2018, which application claims priority or the benefit under 35 U.S.C. 119 of U.S. provisional application No. 62/362,642 filed Jul. 15, 2016, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to a process for retarding the staling of flat breads, as well as flat breads obtainable by the method of the invention.

BACKGROUND OF THE INVENTION

In the bread-making process, it is known to add bread-improving and/or dough-improving additives to the bread dough in order to improve texture, volume, flavor, freshness of the bread, as well as improving machinability of the dough.

In recent years, a number of enzymes have been used as dough and/or bread improving agents.

Various amylases have been suggested for retarding the staling by the addition to dough. For example, WO 91/04669 discloses the use of a maltogenic alpha-amylase from *B. stearothermophilus* to retard staling.

GB 2417184 describes a process for preparation of wheat tortilla comprising using an exoamylase and an emulsifier.

WO 2010/124206 describes the use of raw starch degrading enzymes to retard staling of flat breads.

However, baked products such as flat bread provide additional challenges in retarding staling. For example, many amylases require longer baking times to allow sufficient starch modification and are therefore less suitable to the rapid baking time of flat bread.

There is therefore still a need for finding improved enzyme solutions in flat bread production.

SUMMARY OF THE INVENTION

The present invention relates to a method for improving the rollability of flat breads comprising
  a) adding a maltogenic alpha-amylase and a beta amylase to a flour or to a dough comprising a flour;
  b) making the dough; and
  c) making flat breads from the dough.

In one embodiment, the flat breads are baked; especially the flat breads are baked at a different location than the dough making location.

In one embodiment, the flour according to the present invention is selected from the group consisting of wheat flour, corn flour, rye flour, barley flour, oat flour, rice flour, sorghum flour, soy flour, flour from pulses like gram flour, and a combination thereof.

In a preferred embodiment, the flour according to the present invention is corn flour.

In one embodiment, the maltogenic alpha-amylase according to the invention has at least 70% identity with SEQ ID NO:1.

In one embodiment, the beta amylase according to the invention has at least 70% identity with SEQ ID NO:2.

In one embodiment, the flat bread according to the invention has a rollability at 7 days post baking which is better than the rollability of a flat bread which is prepared under the same conditions, but without treatment with a maltogenic alpha-amylase and a beta-amylase.

In one embodiment, the flat bread according to the invention has a rollability at 14 days post baking which is better than the rollability of a flat bread which is prepared under the same conditions, but without treatment with a maltogenic alpha-amylase and a beta-amylase.

In one embodiment, the flat bread according to the invention has a moistness at 7 days post baking which is better than the moistness of a flat bread which is prepared under the same conditions, but without treatment with a maltogenic alpha-amylase and a beta-amylase.

In one embodiment, the flat bread according to the invention has a moistness at 14 days post baking which is better than the moistness of a flat bread which is prepared under the same conditions, but without treatment with a maltogenic alpha-amylase and a beta-amylase.

In one embodiment, the flat bread according to the invention has a softness at 7 days post baking which is better than the softness of a flat bread which is prepared under the same conditions, but without treatment with a maltogenic alpha-amylase and a beta-amylase.

In one embodiment, the flat bread according to the invention has a softness at 14 days post baking which is better than the softness of a flat bread which is prepared under the same conditions, but without treatment with a maltogenic alpha-amylase and a beta-amylase.

In one embodiment, the dough according to the invention further comprises one or more enzymes selected from the group consisting of amylase, glucanase, galactanase, mannanase, aminopeptidase, alpha-amylase, carboxypeptidase, catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, phospholipase, mannosidase, oxidase, pectinolytic enzymes, peptidoglutaminase, peroxidase, phytase, glucose oxidase, polyphenoloxidase, proteolytic enzyme, ribonuclease, transglutaminase and xylanase.

In one embodiment, the flat breads according to the invention are tortillas; especially corn tortillas.

In one embodiment, we claim a flat bread obtainable by a method of the present invention.

In one embodiment, we claim a flat bread dough composition comprising a maltogenic alpha-amylase and a beta-amylase.

In one embodiment, we claim a flat bread dough premix comprising a maltogenic alpha-amylase, a beta-amylase, and a flour selected from the group consisting of wheat flour, corn flour, rye flour, barley flour, oat flour, rice flour, sorghum flour, soy flour, flour from pulses like gram flour, and a combination thereof.

In one embodiment, we claim a flat bread dough premix comprising a maltogenic alpha-amylase, a beta-amylase, and corn flour.

DETAILED DESCRIPTION OF THE INVENTION

Definitions

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

Variant: The term "variant" means a polypeptide having either maltogenic alpha-amylase activity or beta-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more amino acids adjacent to and immediately following the amino acid occupying a position.

Improved property: When the enzyme composition according to the invention is incorporated into a flour and/or a dough in effective amounts, one or more properties are improved compared to a flour and/or a dough in which the enzyme composition is not added.

The improved property may be determined by comparison of a dough and/or a baked product prepared with and without addition of the enzyme composition of the present invention in accordance with the methods of present invention which are described below. Organoleptic qualities may be evaluated using procedures well established in the baking industry, and may include, for example, the use of a panel of trained taste-testers.

Flat Bread and Flat Bread Dough Compositions

As used herein, "flat bread" means bread prepared from flattened dough, and which typically has a thickness of one millimeter to a few centimeters.

A flat bread may be made from a simple mixture of flour, water, and salt and then thoroughly rolled into flattened dough. Flat breads have a very quick baking time (often <2 minutes).

In one embodiment, the flat bread is unleavened, i.e., made without yeast.

In another embodiment, the flat bread is made with yeast.

The flat bread may include further optional ingredients, such as olive oil, sesame oil, shortenings, spices, garlic, curry powder, diced jalapeños, chili powder, pepper, vegetables, and the like.

Examples of flat breads include tortilla, pita, Arabic bread, Indian flat bread (IFB), wheat and gluten free flat breads. Further non-limiting examples include lavash, baladi, barbari, Sangak, tanoor, taftoon, shami, halabi, mafrood, burr, bairuti, pocket bread, naan, phulka, chapatti, and paratha.

In a particular embodiment, the flat bread product is a tortilla, especially corn tortilla.

As used herein "flat bread dough" means any dough used to prepare a flat bread.

The dough used to prepare a flat bread product may be made from any suitable flour source, e.g., flour sourced from grains, such as, wheat flour, corn flour, rye flour, barley flour, oat flour, rice flour, or sorghum flour, potato flour, soy flour, flour from pulses and combinations thereof; in particular corn flour.

According to the present invention, the corn flour may be produced as known in the art, e.g., to produce nixtamalized corn flour (NCF). Nixtamalized corn flour is produced by the steps of alkaline cooking (heating and steeping) of corn, washing, wet milling the nixtamal, and drying, thereby producing corn masa flour.

Any flat bread process may be used to prepare the flat bread. The process of preparing flat bread generally involves the sequential steps of dough making (with an optional proofing step), sheeting or dividing, shaping or rolling, and proofing the dough, which steps are well known in the art.

In addition to preparing fresh flat bread dough or flat bread products, the present invention is also directed to a method for preparing flat bread dough that can be stored, e.g., at room temperature or with refrigeration, prior to baking. An example of a method for preparing a flat bread dough that can be stored prior to baking includes the steps of making a dough (with an optional proofing), sheeting or dividing, shaping or rolling, proofing, and storing the dough.

In addition to preparing fresh flat bread dough or flat bread products, the present invention is directed to a method for preparing a frozen flat bread dough. The dough is frozen after preparation of the dough comprising the enzyme combination of the present invention (i.e., prior to baking). A frozen flat bread dough may be advantageous for storage and/or distribution. An example of a method for preparing a frozen flat bread dough includes the steps of making a dough (with an optional proofing), sheeting or dividing, shaping or rolling, proofing, and freezing the dough. The present invention is also directed to a frozen flat bread dough comprising the enzyme combination of the present invention.

In one embodiment, the invention provides a method for preparing a flat bread composition, comprising a maltogenic alpha-amylase and a beta amylase.

Industrial Processes

The present invention is particularly useful for preparing flat bread dough and flat bread products in industrialized processes, that is, in which the dough used to prepare flat bread and/or flat bread products are prepared mechanically using automated or semi-automated equipment.

The present invention provides significant advantages in that flat bread can now be prepared using automated or semi-automated processes in which the flat bread is stored for distribution and consumer use more than 24 hours after preparation.

The process of preparing flat bread generally involves the sequential steps of dough making (with optional proofing step(s)), sheeting or dividing, shaping or rolling, and proofing, the dough, which steps are well known in the art. In an industrial flat bread production process according to the present invention, one or more of these steps is/are performed using automated or semi-automated equipment.

The present invention is particularly useful for corn tortilla processing, in particular cold press.

Enzymes
Maltogenic Alpha-Amylase

The maltogenic alpha-amylase according to the invention (EC 3.2.1.133) may be from *Bacillus*. A maltogenic alpha-amylase from *B. stearothermophilus* strain NCIB 11837 is commercially available from Novozymes NS under the tradename NOVAMYL.

Preferably, the maltogenic alpha-amylase is an enzyme having at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 1. Preferably, the maltogenic alpha-amylase is an enzyme having the amino acid sequence shown in SEQ ID NO:1 herein.

The maltogenic alpha-amylase may further comprise one or more additional alterations at one or more (e.g., several) other positions in SEQ ID: 1.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuNal, Ala/Glu, and Asp/Gly.

The maltogenic alpha-amylase may also be a variant of the maltogenic alpha-amylase from *B. stearothermophilus* as disclosed in, e.g., WO1999/043794; WO2006/032281; or WO2008/148845, e.g., Novamyl® 3D available from Novozymes NS.

A maltogenic alpha-amylase is added in an effective amount for retarding the staling of the baked product. The amount will typically be in the range of 0.01-10 mg of enzyme protein per kg of flour, e.g., 0.05-10 mg of enzyme protein per kg of flour.

Beta Amylase

The beta-amylase according to the present invention (EC 3.2.1.2) is preferably selected from the group consisting of a *Bacillus flexus* beta-amylase, a *Clostridium* thermosulphurogenes beta-amylase, a barley beta-amylase, or a wheat beta-amylase. In a preferred embodiment, the beta-amylase is a *Bacillus flexus* beta-amylase.

More particularly, the beta-amylase comprises the polypeptide of SEQ ID NO: 2; or a beta-amylase having at least 70%, at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 2.

The beta amylase may further comprise one or more additional alterations at one or more (e.g., several) other positions in SEQ ID: 2.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

The beta-amylase may be the Secura™ product obtainable from Novozymes NS.

A beta-amylase is added in an effective amount for retarding the staling of the baked product. The amount will typically be in the range of 0.01-10 mg of enzyme protein per kg of flour, e.g., 0.05-10 mg of enzyme protein per kg of flour.

Additional Enzymes

Optionally, one or more additional enzymes, such as amylase, glucanase, galactanase, mannanase, aminopeptidase, alpha-amylase, carboxypeptidase, catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, phospholipase, mannosidase, oxidase, pectinolytic enzymes, peptidoglutaminase, peroxidase, phytase, glucose oxidase, polyphenoloxidase, proteolytic enzyme, ribonuclease, transglutaminase or xylanase may be used together with the enzyme composition according to the invention. The additional enzyme may be of any origin, including mammalian and plant, and preferably of microbial (bacterial, yeast or fungal) origin.

The glucoamylase for use in the present invention include glucoamylases having a sequence identity of at least 50%, at least 60%, at least 65%, at least 70%, at least 75%, at least 80%, at least 85%, at least 90%, at least 95%, at least 96%, at least 97%, at least 98%, or at least 99% to the amino acid sequence of the *A. niger* G1 or G2 glucoamylase (Boel et al. (1984), EMBO J. 3 (5), p. 1097-1102), the *A. awamori* glucoamylase disclosed in WO 84/02921, or the *A. oryzae* glucoamylase (Agric. Biol. Chem. (1991), 55 (4), p. 941-949). A suitable commercial glucoamylase is GoldCrust™ obtainable from Novozymes NS.

Suitable commercial alpha-amylase compositions include, e.g., BAKEZYME P 300 (available from DSM) and FUNGAMYL 2500 SG, FUNGAMYL 4000 BG, FUNGAMYL 800 L, FUNGAMYL ULTRA BG and FUNGAMYL ULTRA SG (available from Novozymes NS).

The glucose oxidase may be a fungal glucose oxidase, in particular an *Aspergillus niger* glucose oxidase (such as GLUZYME®, available from Novozymes NS).

The xylanase which may be of microbial origin, e.g., derived from a bacterium or fungus, such as a strain of *Aspergillus*, in particular of *A. aculeatus, A. niger, A. awamori*, or *A. tubigensis*, from a strain of *Trichoderma*, e.g. *T. reesei*, or from a strain of *Humicola*, e.g., *H. insolens*. Suitable commercially available xylanase preparations for use in the present invention include PANZEA BG, PENTOPAN MONO BG and PENTOPAN 500 BG (available from Novozymes NS), GRINDAMYL POWERBAKE (available from Danisco), and BAKEZYME BXP 5000 and BAKEZYME BXP 5001 (available from DSM).

The protease may be from *Bacillus*, e.g., *B. amyloliquefaciens*.

The phospholipase may have phospholipase A1, A2, B, C, D or lysophospholipase activity; it may or may not have lipase activity. It may be of animal origin, e.g., from pancreas, snake venom or bee venom, or it may be of microbial origin, e.g., from filamentous fungi, yeast or bacteria, such as *Aspergillus* or *Fusarium*, e.g., *A. niger, A. oryzae* or *F. oxysporum*. A preferred lipase/phospholipase from *Fusarium oxysporum* is disclosed in WO 98/26057. Also, the variants described in WO 00/32758 may be used. Suitable phospholipase compositions are LIPOPAN F and LIPOPAN XTRA (available from Novozymes NS) or PANAMORE GOLDEN and PANAMORE SPRING (available from DSM).

Enzyme Treatment

The enzymes are added to the flat bread dough ingredients (i.e., prior to baking or freezing the dough), e.g., indirectly to the dough by adding it to the flour used to prepare the dough, or directly to the dough itself.

The enzymes may be added to flour or dough in any suitable form, such as, e.g., in the form of a liquid, in particular a stabilized liquid, or it may be added to flour or dough as a substantially dry powder or granulate. Granulates may be produced, e.g., as disclosed in U.S. Pat. Nos. 4,106,991 and 4,661,452. Liquid enzyme preparations may, for instance, be stabilized by adding a sugar or sugar alcohol or lactic acid according to established procedures. Other enzyme stabilizers are well-known in the art. The enzyme combination treatment may be added to the flat bread dough ingredients in any suitable manner, such as individual components (separate or sequential addition of the enzymes), or addition of the enzymes together in one step or one composition.

The dough may also comprise other conventional ingredients, e.g., one or more emulsifiers. Emulsifiers serve to improve dough extensibility and may also be of some value for the consistency of the resulting flat bread, as well as for its storage stability and handling. Examples of suitable emulsifiers are mono- or diglycerides, polyoxyethylene stearates, diacetyl tartaric acid esters of monoglycerides, sugar esters of fatty acids, propylene glycol esters of fatty acids, polyglycerol esters of fatty acids, lactic acid esters of monoglycerides, acetic acid esters of monoglycerides, lecithin or phospholipids, or ethoxylated monoglycerides. Particular emulsifiers include monoglycerides, diacetyl tartaric acid esters of monoglyceride (DATEM) and sodium stearoyl lactylate (SSL).

Other conventional ingredients include proteins, such as milk powder, gluten, and soy; eggs (either whole eggs, egg yolks or egg whites); an oxidant such as ascorbic acid, potassium bromate, potassium iodate, azodicarbonamide (ADA), ammonium persulfate or potassium persulphate; an amino acid such as L-cysteine; a sugar such as sucrose, dextrose, etc.; a salt such as sodium chloride, calcium acetate, sodium sulfate or calcium sulfate, diluents such silica dioxide, starch of different origins. Still other convention ingredients include hydrocolloids such as CMC, guar gum, xanthan gum, locust bean gum, etc. Modified starches may be also used.

Pre-Mixes

It will often be advantageous to provide the enzymes used in the treatment of the present invention in admixture with other ingredients used to improve the properties of flat bread products. These are commonly known in the art as "pre-mixes," which usually comprise flour.

Hence, in a further aspect, the present invention relates to a flat bread premix for improving the quality of dough used to prepare a flat bread product or flat bread products, which premix comprises a maltogenic alpha-amylase and a beta amylase and one or more flat bread dough ingredients, in particular flour such as flour from grains, such as, wheat flour, corn flour, rye flour, barley flour, oat flour, rice flour, sorghum flour, soy flour, or flour from pulses like gram flour, and combinations thereof. In a preferred embodiment, the flour is corn flour.

In another embodiment, the present invention relates to a flat bread pre-mix comprising the enzyme combinations of the present invention and flour, such as, flour from grains, such as, wheat flour, corn flour, rye flour, barley flour, oat flour, rice flour, sorghum flour, and combinations thereof, and one or more additional enzymes, as previously described.

The pre-mix composition may be in liquid form or dry or substantially dry form.

Dough and Flat Bread Properties

In one embodiment, the flat bread prepared by the methods and compositions of the invention provides improved storage properties. The flat bread prepared by the methods and compositions of the present invention are used as anti-staling agents to improve the shelf life of the flat bread product. The anti-staling effect (and improved shelf life) of a flat bread product can be determined by a number of methods well known in the art.

Primarily anti-staling effectiveness is measured by the hardness (also referred to as "firmness" and the opposite of "softness") of the flat bread product. Hardness can be measured using a texture profile analyzer. Texture measurements for flat bread such as tortilla can be measured according to methods known in the art as disclosed in e.g., Gomez-Mendez et al. "Instrumental and sensory techniques for the measurement of wheat tortilla texture." IFT Conference Paper, New Orleans (1996) and Mao, "Texture measurements of commercially available wheat flour tortillas." Poster presented at IFT Annual Meeting, Dallas, USA (Jun. 10-14, 2000).

Besides hardness/softness, stickiness, extensibility and elasticity are also important quality parameters for flat bread. Other important properties include rollability, foldability, flexibility, layering, bite and/or texture.

Other tests known in the art may be used to assess the shelf life and other organoleptic qualities of the flat bread prepared by the methods and compositions of the present invention.

Storage/Shelf Life

In one embodiment, the present invention relates to a flat bread having an improved shelf life at least 1 hour after baking. In one embodiment, the present invention relates to a flat bread having an improved shelf life at least 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours or 23 hours after baking. In one embodiment, the present invention relates to a flat bread having an improved shelf life at least 24 hours after baking. In another embodiment, the present invention relates to a flat bread having an improved shelf life at least 48 hours after baking. In another embodiment, the present invention relates to a flat bread having an improved shelf life at least 72 hours after baking. In another embodiment, the present invention relates to a flat bread having an improved shelf life at least 96 hours after baking. In another embodiment, the present invention relates to a flat bread having an improved shelf life at least 120 hours after baking. In another embodiment, the present invention relates to a flat bread having an improved shelf life at least 6 days, 7 days, 8 days, 9 days, 10 days, 11 days, 12 days, 13 days, 14 days, 15 days, 16 days, 17 days, 18 days, 19 days, 20 days or 21 days after baking.

Shelf life can be measured as follows: A flat bread is prepared using enzyme compositions of the present invention and compared to a control flat bread, that is, a flat bread prepared in the same way but without enzyme compositions of the present invention.

The flat bread is stored in a sealed plastic bag at 25° C. After the storage period, (e.g., 1 hour, 24 hours, 48 hours, 72 hours, 96 hours, 7 days, 21 days etc.), the hardness of the flat bread is measured using a texture analyzer and compared to a control flat bread stored under identical conditions. An improved shelf life is defined as a flat bread which is less hard (i.e., softer) than the control as measured by the texture analyzer.

In addition to preparing fresh flat bread dough or flat bread products, the present invention is directed to a method for preparing flat bread dough that can be stored, e.g., at room temperature or with refrigeration, or frozen prior to baking. The dough can be stored and/or frozen after preparation of the dough and treatment by the enzyme combinations of the present invention (i.e., prior to baking) for 1 hour, 24 hours, 48 hours, 72 hours, 96 hours, 5 days, 6 days, 7 days, 8 days, 9 days, 10 days, 11 days, 12 days, 13 days, 14 days, 15 days, 16 days, 17 days, 18 days, 19 days, 20 days, 21 days, etc.

In one embodiment, the flat bread is also compared to a control in other quality parameters, such as, stickiness, extensibility, elasticity, rollability, foldability, flexibility, layering, bite and texture; especially rollability. The flat bread prepared by the enzyme treatment of the present invention is analyzed at a time after baking or during storage (e.g., 1 hour after baking and/or 24 hours, 48 hours, 72 hours, 96 hours, 7 days, 14 days, 21 days, etc. post baking).

The flat bread prepared by the enzyme treatment of the present invention preferably has improved qualities in terms of improved stickiness, extensibility, elasticity, rollability, flexibility, foldability, layering, bite and/or texture; especially improved rollability as compared to treatment with other anti-staling enzymes.

The flat bread may be prepared with other background enzymes.

The invention described and claimed herein is not to be limited in scope by the specific embodiments herein disclosed, since these embodiments are intended as illustrations of several aspects of the invention. Any equivalent embodiments are intended to be within the scope of this invention as well as combinations of one or more of the embodiments. Various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties. The present invention is further described by the following examples which should not be construed as limiting the scope of the invention. For example, routine modifications to optimize the methods of enzymatic modification according to the present invention are contemplated.

EXAMPLES

Example 1

Rollability of Corn Tortillas
Corn tortillas were made in the following way:
Mixture I:
0.5 kg corn masa flour;
40 ppm Novamyl 10000 BG;
and 0.6 kg water were mixed for 5 minutes.
Mixture II:
0.5 kg corn masa flour;
460 ppm Secura;
and 0.6 kg water were mixed for 5 minutes.
Mixture III:
0.5 kg corn masa flour;
40 ppm Novamyl 10000 BG and 460 ppm Secura;
and 0.6 kg water were mixed for 5 minutes.
40 g dough balls were made from the above mixture(s).
The dough balls rested for 5 minutes at room temperature (covered with plastic).
The dough balls were shaped into thin circular disk using a cold pressing technique.
The thin disk of dough had a diameter of 18 cm.
The thin disk of dough was baked for 1 min. into tortillas (30 sec. for each side).
The tortillas were cooled for 15 min.
The tortillas were evaluated at day 1, day 7, and day 14 (after baking).
10 trained people evaluated the tortillas.

TABLE 1

Results

| Enzyme | Rollability scores at day 1; day 7; and day 14<br>Scoring 1-5:<br>1 very easy to break when it is rolled; and 5 being very flexible to roll without any cracks |
|---|---|
| Day 1 | |
| maltogenic alpha-amylase | 3.88 |
| beta amylase | 4.00 |
| maltogenic alpha-amylase + beta amylase | 3.85 |
| Day 7 | |
| maltogenic alpha-amylase | 2.37 |
| beta amylase | 2.72 |
| maltogenic alpha-amylase + beta amylase | 3.24 |
| Day 14 | |
| maltogenic alpha-amylase | 1.93 |
| beta amylase | 2.38 |
| maltogenic alpha-amylase + beta amylase | 2.78 |

CONCLUSION

The rollability of the tortillas made with the mixture of maltogenic alpha-amylase and beta-amylase is surprisingly good after 7 days and 14 days, compared with the rollability of the tortillas made with maltogenic alpha-amylase alone, or beta-amylase alone.

---

The invention claimed is:

1. A method for producing a tortilla comprising
    a) adding a maltogenic alpha-amylase and a beta-amylase to a corn flour or to a dough comprising a corn flour;
    b) making the dough; and
    c) making the tortilla from the dough;
wherein the tortilla has a rollability at 7 days post baking which is better than the rollability of a tortilla which is prepared under the same conditions, but without treatment with a maltogenic alpha-amylase and a beta-amylase, at 7 days post baking.

2. The method according to claim 1, wherein the tortilla is baked.

3. The method according to claim 1, wherein the maltogenic alpha-amylase has at least 90% identity with SEQ ID NO:1.

4. The method according to claim 1, wherein the beta-amylase has at least 90% identity with SEQ ID NO:2.

5. The method according to claim 1, wherein additionally the tortilla has a moistness at 7 days post baking which is better than the moistness of a tortilla which is prepared under the same conditions, but without treatment with a maltogenic amylase and a beta-amylase.

6. The method according to claim 1, wherein additionally the tortilla has a softness at 7 days post baking which is better than the softness of a tortilla which is prepared under the same conditions, but without treatment with a maltogenic alpha-amylase and a beta-amylase.

7. The method according to claim 1, wherein the dough further comprises one or more enzymes selected from the group consisting of amylase, glucanase, galactanase, mannanase, aminopeptidase, alpha-amylase, carboxypeptidase, catalase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, phospholipase, mannosidase, oxidase, pectinolytic enzymes, peptidoglutaminase, peroxidase, phytase, glucose oxidase, polyphenoloxidase, proteolytic enzyme, ribonuclease, transglutaminase and xylanase.

8. The method according to claim 1, wherein the maltogenic alpha-amylase has at least 95% identity with SEQ ID NO: 1 and the beta-amylase has at least 95% identity with SEQ ID NO: 2.

9. The method according to claim 1, wherein the maltogenic alpha-amylase has at least 97% identity with SEQ ID NO: 1 and the beta-amylase has at least 97% identity with SEQ ID NO: 2.

10. The method according to claim 1, wherein the maltogenic alpha-amylase comprises SEQ ID NO: 1 and the beta-amylase comprises SEQ ID NO: 2.

* * * * *

SEQUENCE LISTING

<160> NUMBER OF SEQ ID NOS: 2

<210> SEQ ID NO 1
<211> LENGTH: 686
<212> TYPE: PRT
<213> ORGANISM: Bacillus stearothermophilus

<400> SEQUENCE: 1

```
Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
    210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
    290                 295                 300

Asn Asn Met Val Asn Gln Thr Gly Asn Glu Tyr Lys Tyr Lys Glu Asn
305                 310                 315                 320
```

```
Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365

Gly Gly Asn Asp Pro Tyr Asn Arg Gly Met Met Pro Ala Phe Asp Thr
    370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Gln Arg Trp Ile Asn
            405                 410                 415

Asn Asp Val Tyr Ile Tyr Glu Arg Lys Phe Phe Asn Asp Val Val Leu
            420                 425                 430

Val Ala Ile Asn Arg Asn Thr Gln Ser Ser Tyr Ser Ile Ser Gly Leu
            435                 440                 445

Gln Thr Ala Leu Pro Asn Gly Ser Tyr Ala Asp Tyr Leu Ser Gly Leu
    450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
            500                 505                 510

Asn Val Val Thr Ile Asp Gly Lys Gly Phe Gly Thr Thr Gln Gly Thr
            515                 520                 525

Val Thr Phe Gly Gly Val Thr Ala Thr Val Lys Ser Trp Thr Ser Asn
    530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
            580                 585                 590

Pro Thr Asn Leu Gly Asp Lys Ile Tyr Leu Thr Gly Asn Ile Pro Glu
        595                 600                 605

Leu Gly Asn Trp Ser Thr Asp Thr Ser Gly Ala Val Asn Asn Ala Gln
    610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
            660                 665                 670

Pro Thr Gly Ala Thr Gly Asn Ile Thr Val Thr Trp Gln Asn
        675                 680                 685

<210> SEQ ID NO 2
<211> LENGTH: 515
<212> TYPE: PRT
<213> ORGANISM: Bacillus flexus

<400> SEQUENCE: 2

Ala Val Asn Gly Gln Ser Phe Asn Ser Asn Tyr Lys Thr Tyr Leu Met
1               5                   10                  15
```

Ala Pro Leu Lys Lys Val Thr Glu Phe Thr Thr Trp Glu Ala Phe Glu
            20                  25                  30

Asn Asp Leu Arg Lys Ala Lys Gln Asn Gly Phe Tyr Ala Val Thr Val
            35                  40                  45

Asp Phe Trp Trp Gly Asp Met Glu Lys Asn Gly Asp Gln Gln Phe Asp
50                  55                  60

Phe Ser Tyr Ala Gln Arg Phe Ala Gln Ala Ala Arg Asn Ala Gly Ile
65                  70                  75                  80

Lys Met Val Pro Ile Ile Ser Thr His Gln Cys Gly Gly Asn Val Gly
                85                  90                  95

Asp Asp Cys Asn Thr Pro Leu Pro Ser Trp Ile Trp Asn Thr Lys Thr
            100                 105                 110

Asp Asp Ser Leu Tyr Phe Lys Ser Glu Thr Gly Thr Val Asn Lys Glu
            115                 120                 125

Thr Val Asn Pro Leu Ala Thr Asp Val Ile Thr Lys Gln Tyr Gly Glu
130                 135                 140

Leu Tyr Thr Ala Phe Ala Gln Ala Leu Ala Pro Tyr Lys Asp Val Ile
145                 150                 155                 160

Pro Lys Val Tyr Leu Ser Gly Gly Pro Ala Gly Glu Leu Arg Tyr Pro
                165                 170                 175

Ser Tyr Thr Ala Ala Asp Gly Thr Gly Tyr Pro Ser Arg Gly Lys Phe
            180                 185                 190

Gln Ala Tyr Thr Asp Phe Ala Lys Ser Lys Phe Gln Met Trp Ala Val
            195                 200                 205

Asn Lys Tyr Gly Ser Leu Ala Gly Val Asn Gln Ala Trp Gly Leu Ser
210                 215                 220

Leu Thr Ser Thr Ser Gln Ile Leu Pro Pro Ser Asp Gly Asn Gln Phe
225                 230                 235                 240

Leu Lys Asp Gly Tyr Asn Thr Asn Tyr Gly Lys Asp Phe Leu Glu Trp
                245                 250                 255

Tyr Gln Gly Val Leu Gln Asp His Ala Lys Arg Ile Gly Ala Leu Ala
            260                 265                 270

His Gln Ala Phe Asp Pro Val Phe Asn Val Pro Val Gly Ala Lys Ile
            275                 280                 285

Ala Gly Ile His Trp Gln Tyr Asn Asn Pro Thr Met Pro His Ala Ala
290                 295                 300

Glu Lys Pro Ala Gly Tyr Asn Asn Tyr Ser Thr Leu Leu Asp Ser Phe
305                 310                 315                 320

Lys Thr Ala Lys Leu Asp Leu Thr Phe Thr Cys Leu Glu Met Val Asp
                325                 330                 335

Ser Gly Thr Tyr Pro Glu Tyr Ser Met Pro Lys Thr Leu Val Lys Glu
            340                 345                 350

Val Ala Ser Leu Ala Asn Ala Lys Gly Ile Val Leu Asn Gly Glu Asn
            355                 360                 365

Ala Leu Ser Ile Gly Ser Glu Glu Gln Tyr Lys Arg Ala Ala Glu Met
370                 375                 380

Thr Phe Asn Tyr Asn Phe Ala Gly Phe Thr Leu Leu Arg Phe Tyr Asp
385                 390                 395                 400

Val Ile Asn Asn Ser Thr Arg Met Ser Gln Phe Asn Gln His Leu Asn
                405                 410                 415

Ile Lys Pro Val Ala Gln Thr Met Val Val Lys Asn Ala Pro Thr Ser
            420                 425                 430

```
Ser Gly Glu Ser Val Tyr Ile Val Gly Asp Arg Pro Glu Leu Gly Gln
        435                 440                 445

Trp Asp Thr Ile Ala Tyr Pro Ile Lys Leu Ser Tyr Asn Ser Thr Tyr
    450                 455                 460

Gly Asp Trp Arg Gly Thr Val Asn Phe Pro Ala Asp Arg Ser Val Gln
465             470                 475                 480

Phe Lys Ala Ile Ile Lys Arg Ser Asp Gly Ser Leu Lys Ser Trp Gln
            485                 490                 495

Pro Thr Gln Gln Tyr Trp Asn Val Pro Gly Thr Pro Thr Thr Tyr Thr
            500                 505                 510

Asn Asn Trp
        515
```